United States Patent
Lange et al.

(10) Patent No.: US 7,342,032 B2
(45) Date of Patent: Mar. 11, 2008

(54) THIAZOLE DERIVATIVES HAVING $CB_1$-ANTAGONISTIC, AGONISTIC OR PARTIAL AGONISTIC ACTIVITY

(75) Inventors: Josephus H. M. Lange, Weesp (NL); Cornelis G. Kruse, Weesp (NL); Arnoldus H. J. Herremans, Weesp (NL); Herman H. van Stuivenberg, Weesp (NL); Jessica A. R. Dijksman, Weesp (NL); Andrew C. McCreary, Weesp (NL)

(73) Assignee: Solvay Pharmaceuticals, Inc., Weesp (NL)

(*) Notice: Subject to any disclaimer, the term of this patent is extended or adjusted under 35 U.S.C. 154(b) by 452 days.

(21) Appl. No.: 10/490,546

(22) PCT Filed: Mar. 17, 2003

(86) PCT No.: PCT/EP03/50063
§ 371 (c)(1),
(2), (4) Date: Mar. 23, 2004

(87) PCT Pub. No.: WO03/078413
PCT Pub. Date: Sep. 25, 2003

(65) Prior Publication Data
US 2004/0266841 A1 Dec. 30, 2004

(30) Foreign Application Priority Data
Mar. 18, 2002 (EP) .................................. 02076481

(51) Int. Cl.
*A61K 31/426* (2006.01)
*C07D 277/56* (2006.01)

(52) U.S. Cl. ....................... 514/365; 548/200; 548/201

(58) Field of Classification Search ................ 548/200, 548/201
See application file for complete search history.

(56) References Cited

U.S. PATENT DOCUMENTS

| 5,229,386 | A | 7/1993 | Takasugi et al. |
| 5,624,941 | A | 4/1997 | Barth et al. |
| 2005/0065189 | A1 | 3/2005 | Lange et al. |
| 2005/0124660 | A1 | 6/2005 | Antel et al. |

FOREIGN PATENT DOCUMENTS

| CN | 1043936 A | 7/1990 |
| EP | 0 377 457 A1 | 7/1990 |
| WO | WO 00/46209 | 8/2000 |
| WO | WO 01/66540 A1 | 9/2001 |

OTHER PUBLICATIONS

McLaughlin et al. Psychopharmacology 2005, 180, 286-293.*
Carai et al. CNS Drug Review 2006, 12(2), 91-99.*
Gardiner et al. British Journal of Pharmacology 2002, 136, 581-587.*
Pertwee, Roger G., "Pharmacology of Cannabinoid Receptor Ligands", Current Medicinal Chemistry, vol. 6, pp. 635-664, (1999).

* cited by examiner

*Primary Examiner*—Rebecca Anderson
*Assistant Examiner*—Jason M Nolan
(74) *Attorney, Agent, or Firm*—Finnegan, Henderson, Farabow, Garrett & Dunner, L.L.P.

(57) ABSTRACT

Computer game systems respond to the spatial state of a pointing device. Changes in the spatial state of a hand held or mobile unit, or plurality of units drive a game scheme maintained in a computer. Position and attitude of the mobile device cause program branching functions which are bases upon a game rule set. In example, a game scheme executed on a computing apparatus may be incorporated into a mobile telephone having a GPS and electronic compass. Physical states relating to position and pointing attitude of the telephone as described in part by position or attitude parameters, drives computer programming code to takes actions which depend on measured position and attitude values thus making computer games for mobile users are made highly interactive. User gestures including simple pointing actions allow a user to express desires to a computer in an express and direct fashion. These games have many features which cannot be found in more traditional handheld computer games which do not take into consideration the spatial state of an object controlled by a player-user

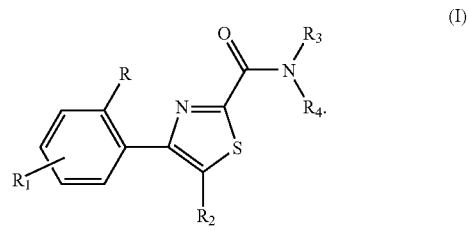

(I)

9 Claims, No Drawings

THIAZOLE DERIVATIVES HAVING CB₁-ANTAGONISTIC, AGONISTIC OR PARTIAL AGONISTIC ACTIVITY

The present invention relates to a group of thiazole derivatives, to methods for the preparation of these compounds, and to pharmaceutical compositions containing one or more of these compounds as an active component.

The above mentioned thiazole derivatives are potent cannabinoid ($CB_1$) receptor antagonists, $CB_1$ receptor agonists or $CB_1$ receptor partial agonists, with utility for the treatment of psychiatric and neurological disorders and other diseases involving cannabinoid $CB_1$ neurotransmission.

4,5-Diarylthiazole derivatives have been described in EP 388909 and EP 377457 as 5-lipoxygenase inhibitors for the treatment of thrombosis, hypertension, allergy and inflammation. The exemplified structures therein all contain two phenyl rings which are p-substituted with a methoxy, fluoro, methylthio or methylsulfinyl group. WO 9603392 describes sulfonylaryl-arylthiazoles for inflammation and pain, arthritis or fever as inflammation-associated disorders. JP 05345772 relates to 4,5-diarylthiazoles as acetyl cholinesterase inhibitors, and JP 04154773 describes 4,5-diarylthiazoles having analgesic, antiinflammatory and antipyretic action.

It has now surprisingly been found that the 4,5-diarylthiazole derivatives of the formula (I), pro-drugs thereof and salts thereof

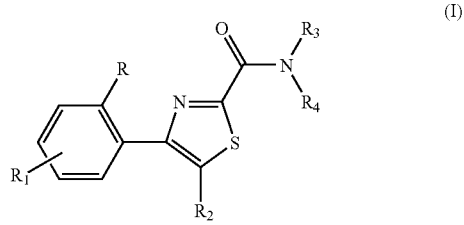

(I)

wherein
R represents a hydrogen atom or a substituent X from the group branched or unbranched $C_{1-3}$-alkyl or alkoxy, hydroxy, halogen, trifluoromethyl, trifluoromethylthio, trifluoromethoxy, nitro, amino, mono- or dialkyl ($C_{1-2}$)-amino, mono- or dialkyl ($C_{1-2}$)-amido, branched or unbranched ($C_{1-3}$)-alkoxycarbonyl, trifluoromethylsulfonyl, sulfamoyl, branched or unbranched alkyl ($C_{1-3}$)sulfonyl, carboxyl, cyano, carbamoyl, branched or unbranched dialkyl($C_{1-3}$) aminosulfonyl, branched or unbranched monoalkyl($C_{1-3}$)-aminosulfonyl and acetyl, $R_1$ is a hydrogen atom or represents 1-4 substituents X, wherein X has the abovementioned meaning, $R_2$ represents a phenyl, thienyl, pyridyl or pyrimidinyl group, which groups may be substituted with 1-4 substituents X, wherein X has the abovementioned meaning or $R_2$ represents naphtyl, $R_3$ represents a hydrogen atom or a branched or unbranched $C_{1-10}$ alkyl or cycloalkyl-alkyl group or a phenyl, benzyl or phenethyl group which aromatic rings may be substituted with 1-5 substituents Z, which can be the same or different, from the group branched or unbranched $C_{1-3}$-alkyl or alkoxy, hydroxy, halogen, trifluoromethyl, trifluoromethylthio, trifluoromethoxy, nitro, amino, mono- or dialkyl ($C_{1-2}$)-amino, mono- or dialkyl ($C_{1-2}$)-amido, branched or unbranched ($C_{1-3}$)-alkylsulfonyl, dimethylsulfamido, branched or unbranched $C_{1-3}$-alkoxycarbonyl, carboxyl, trifluoromethylsulfonyl, cyano, carbamoyl, sulfamoyl and acetyl, or $R_3$ represents a pyridyl or thienyl group, $R_4$ represents branched or unbranched $C_{1-10}$ alkyl or cycloalkyl-alkyl group, branched or unbranched $C_{1-10}$ alkoxy, $C_{3-8}$ cycloalkyl, $C_{5-10}$ bicycloalkyl, $C_{6-10}$ tricycloalkyl, branched or unbranched $C_{3-10}$ alkenyl, $C_{5-8}$ cycloalkenyl, which groups may contain one or more heteroatoms from the group (O, N, S) and which groups may be substituted with a hydroxy group, 1-3 methyl groups, an ethyl group or 1-3 fluoro atoms, or $R_4$ represents a phenyl, benzyl or phenethyl group which aromatic rings may be substituted with 1-5 substituents Z, wherein Z has the abovementioned meaning, or $R_4$ represents a pyridyl or thienyl group, or $R_4$ represents a group $NR_5R_6$ wherein $R_5$ and $R_6$ together with the nitrogen atom to which they are attached form a saturated or unsaturated, monocyclic or bicyclic, heterocyclic group having 4 to 10 ring atoms, which heterocyclic group contains one or more heteroatoms from the group (O, N, S) and which heterocyclic group may be substituted with a branched or unbranched $C_{1-3}$ alkyl, hydroxy or trifluoromethyl group or a fluoro atom, or $R_3$ and $R_4$—together with the nitrogen atom to which they are attached—form a saturated or unsaturated, monocyclic or bicyclic, heterocyclic group having 4 to 10 ring atoms, which heterocyclic group contains one or more heteroatoms from the group (O, N, S) and which heterocyclic group may be substituted with a branched or unbranched $C_{1-3}$ alkyl, hydroxy or trifluoromethyl group or a fluoro atom, are potent antagonists, agonists or partial agonists of the cannabinoid $CB_1$ receptor.

A pro-drug is an inactive compound, which when absorbed into an active form (Medicinal Chemistry: Principles and Practice, 1994, ISBN 0-85186-494-5, Ed.: F. D. King, p. 216).

Due to the potent $CB_1$ receptor activity the compounds according to the invention are suitable for use in the treatment of psychiatric disorders such as psychosis, anxiety, depression, attention deficits, memory disorders, cognitive disorders, appetite disorders, obesity, addiction, appetence, drug dependence and neurological disorders such as neurodegenerative disorders, dementia, dystonia, muscle spasticity, tremor, epilepsy, multiple sclerosis, traumatic brain Injury, stroke, Parkinson's disease, Alzheimer's disease, epilepsy, Huntington's disease, Tourette's syndrome, cerebral ischaemia, cerebral apoplexy, craniocerebral trauma, stroke, spinal cord injury, neuroinflammatory disorders, plaque sclerosis, viral encephalitis, demyelinisation related disorders, as well as for the treatment of pain disorders, including neuropathic pain disorders, and other diseases involving cannabinoid neurotransmission, including the treatment of septic shock, glaucoma, cancer, diabetes, emesis, nausea, asthma, respiratory diseases, gastrointestinal disorders, gastric ulcers, diarrhoea and cardiovascular disorders.

The affinity of the compounds of the invention for cannabinoid $CB_1$ receptors was determined using membrane preparations of Chinese hamster ovary (CHO) cells in which the human cannabinoid $CB_1$ receptor is stably transfected in conjunction with [³H]CP-55,940 as radioligand. After incubation of a freshly prepared cell membrane preparation with the [³H]-ligand, with or without addition of compounds of the invention, separation of bound and free ligand was performed by filtration over glassfiber filters. Radioactivity on the filter was measured by liquid scintillation counting.

The cannabinoid $CB_1$ receptor antagonistic, agonistic or partial agonistic activity of compounds of the invention was determined by functional studies using CHO cells in which human cannabinoid $CB_1$ receptors are stably expressed. Adenylyl cyclase was stimulated using forskolin and measured by quantifying the amount of accumulated cyclic AMP. Concomitant activation of $CB_1$ receptors by $CB_1$ receptor agonists (e.g. CP-55,940 or (R)-WIN-55,212-2) can attenuate the forskolin-induced accumulation of cAMP in a concentration-dependent manner. This $CB_1$ receptor-mediated response can be antagonised by $CB_1$ receptor antagonists or partial agonists such as the compounds of the invention.

Cannabinoid receptor agonistic or partial agonistic activity of compounds of the invention can be determined according to published methods, such as assessment of in vivo cannabimimetic effects (Wiley, J. L. et al., *J. Pharmacol. Exp. Ther.* 2001, 296, 1013).

Cannabinoid receptor antagonists may behave as inverse agonists (Landsman, R. S. et al., *Eur. J. Pharmacol.* 1997, 334, R1-R2).

The invention relates both to racemates, mixtures of diastereomers and the individual stereoisomers of the compounds having formula (I).

The compounds of the invention can be brought into forms suitable for administration by means of usual processes using auxiliary substances and/or liquid or solid carrier materials.

A suitable synthesis for the compounds according to the present invention is the following:

Synthesis Route A

Step 1 of Route A

Ester hydrolysis of a compound having formula (II) wherein $R_7$ represents a branched or unbranched alkyl group ($C_{1-4}$) or benzyl group.

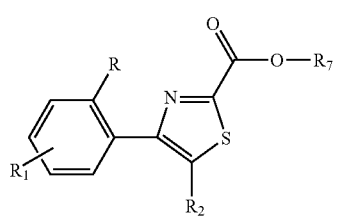

(II)

This reaction gives a compound having formula (III)

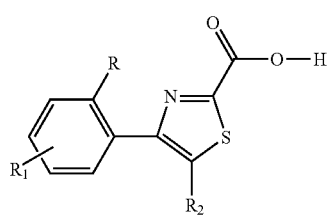

(III)

wherein R, $R_1$ and $R_2$ have the meanings as described hereinabove.

The compounds of the invention having formula (II), wherein $R_7$ represents a branched or unbranched alkyl group ($C_{1-4}$) or benzyl group can be obtained according to methods known, for example:
a) Organic Reactions, Vol. VI, (1951), p. 367409, Ed. R. Adams, John Wiley and Sons Inc., New York
b) J. S. Carter et al., *Bioorg. Med. Chem. Lett.* (1999), 9, 1167-1170
c) T. T. Sakai et al., *Bioorg. Med. Chem.* (1999), 7, 1559-1566
d) A. Tanaka et al., *J. Med. Chem.* (1994), 37, 1189-1199
e) J. J. Talley et al., WO 9603392: Chem. Abstr. 125, 33628
f) V. Cecchetti et al., *Bioorg. Med. Chem.* (1994), 2, 799-806

Step 2 of Route A

Reaction of a compound having formula (III) with a compound having formula $R_3R_4NH$ wherein $R_3$ and $R_4$ have the meanings as described hereinabove via activating and coupling methods such as formation of an active ester, or in the presence of a so-called coupling reagent, such as for example, DCC, HBTU, BOP, CIP (2-chloro-1,3-dimethylimidazolinium hexafluorophosphate), PyAOP (7-azabenzotriazol-1-yloxytris(pyrrolidino)phosphonium hexafluorophosphate) and the like. (For more information on activating and coupling methods see a) M. Bodanszky, A. Bodanszky: The Practice of Peptide Synthesis, Springer-Verlag, New York, 1994; ISBN: 0-387-57505-7; b) K. Akaji et al., *Tetrahedron Lett.* (1994), 35, 3315-3318; c) F. Albericio et al., *Tetrahedron Lett.* (1997), 38, 4853-4856).

This reaction gives a desired thiazole derivative having formula (I).

Alternatively, a compound having formula (III) is reacted with a so-called halogenating agent such as for example thionyl chloride ($SOCl_2$). This reaction gives the corresponding carbonyl chloride (IV).

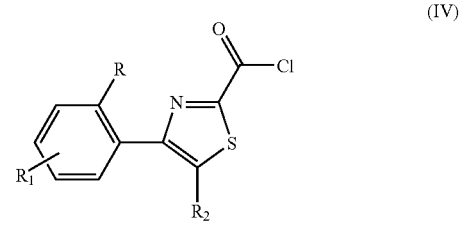

(IV)

Reaction of a compound having formula (IV) with a compound having formula $R_3R_4NH$ wherein wherein $R_3$ and $R_4$ have the meanings as described hereinabove gives a thiazole derivative having formula (I). This reaction is preferably carried out in the presence of an organic base such as for example diisopropylethylamine (DIPEA) or triethylamine.

Alternatively, a compound having formula (II) is reacted in a so-called amidation reaction with a compound having formula $R_3R_4NH$ wherein $R_3$ and $R_4$ have the meanings as described hereinabove to give a thiazole derivative having formula (I). Such amidation reactions can be promoted by the use of trimethylaluminum $Al(CH_3)_3$ (For more information on aluminum-mediated conversion of esters to amides, see: J. I. Levin, E. Turos, S. M. Weinreb, *Synth Commun.* (1982), 12, 989-993.)

Alternatively, a compound having formula $R_3R_4NH$ can be reacted with a strong 30 base, such as lithium diisopropylamide (LDA), lithium hexamethyldisilazide (LiHMDS), potassium hexamethyldisilazide (KHMDS) or sodium hexamethyldisilazide (NaHMDS) and the like to give in situ a compound having formula $R_3R_4NLi$, $R_3R_4NK$ or $R_3R_4NNa$, respectively, which can then be reacted with a compound having formula (II) to give a thiazole derivative having formula (I).

Alternatively, a compound having formula (I) wherein $R_3$ and $R_4$ represent a hydrogen atom can be reacted with a strong base, such as LDA, LiHMDS, NaH and the like, followed by a reaction with a compound L-$R_4$ wherein L represents a so-called leaving group such as Br, Cl, I and the like, and $R_4$ represents a branched or unbranched $C_{1-10}$ alkyl group, cycloalkyl-alkyl group or a branched or unbranched $C_{3-10}$ alkenyl group, which groups may contain one or more heteroatoms from the group (O, N, S) and which groups may be substituted with 1-3 methyl groups, an ethyl group or 1-3 fluoro atoms.

EXAMPLE 1

Part A: Magnesium (3.04 gram, 0.125 mol) is suspended in anhydrous diethyl ether (500 mL) under a nitrogen atmosphere and an iodine crystal is added. A solution of 4-chlorobenzyl chloride (20.12 gram, 0.125 mol) in anhydrous diethyl ether (100 mL) is slowly added to maintain a gentle reflux. After cooling the resulting mixture to room temperature a solution of 2,4-dichlorobenzonitrile (17.2 gram, 0.10 mol) in toluene (100 mL) is slowly added. Temperature is raised to 135° C. and the diethyl ether is removed by distillation, toluene is added and the resulting mixture is refluxed for two additional hours. After cooling to room temperature a solution of HCl (1N, 400 mL) is slowly added under cooling and stirring. The resulting mixture is extracted twice with diethyl ether, dried over $MgSO_4$, filtered and concentrated in vacuo. Flash chromatography (dichloromethane) gives 2-(4-chlorophenyl)-1-(2,4-dichlorophenyl)ethanone as a yellow oil (19.96 gram, 67% yield). Crystallisation from cyclohexane gives pure 2-(4-chlorophenyl)-1-(2,4-dichlorophenyl)ethanone. Melting point: 65-66° C. $^1$H-NMR (200 MHz, $CDCl_3$): δ 7.02-7.45 (m, 7H), 4.22 (s, 2H).

Part B: To a solution of 2-(4-chlorophenyl)-1-(2,4-dichlorophenyl)ethanone (2.82 gram, 9.42 mmol) in benzene (25 mL) is added bromine (0.48 mL, 1.49 gram, 9.31 mmol) and the resulting solution is stirred at room temperature for two hours. Dichloromethane is added and the resulting solution is washed with aqueous $NaHCO_3$ solution. The organic layer is dried over $MgSO_4$, filtered and evaporated in vacuo to give 3.55 gram (quantitative yield) of 2-bromo-2-(4-chlorophenyl)-1-(2,4-dichlorophenyl)ethanone as a yellow oil (purity~95% according to HPLC analysis). $^1$H-NMR (200 MHz, $CDCl_3$): δ 7.00-7.50 (m, 7H), 6.16 (s, 1H).

Analogously was prepared:
2-Bromo-1-(4-chlorophenyl)-2-(2,4-dichlorophenyl) ethanone. $^1$H-NMR (200 MHz, $CDCl_3$): δ 7.95 (d, J=8 Hz, 2H), 7.23-7.62 (m, 5H), 6.77 (s, 1H).

Part C; 2-Bromo-2-(4-chlorophenyl)-1-(2,4-dichlorophenyl)ethanone (9.83 gram, 26.0 mmol) and ethyl thiooxamate (5.28 gram, 39.6 mmol) are dissolved in absolute ethanol (50 mL). The resulting red solution is heated at reflux temperature for 4 hours. After evaporation in vacuo the crude red material (14 gram) is suspended in a mixture of dichloromethane and methyl-tert-butyl ether. The formed solids are removed by filtration. The resulting filtrate is purified by column chromatography (eluant: dichloromethane: $R_f$~0.4) to give ethyl-5-(4-chlorophenyl)-4-(2,4-dichlorophenyl) thiazole-2-carboxylate as a yellow oil (5.21 gram, 48% yield) which slowly solidifies. Melting point: 117-118° C. $^1$H-NMR (200 MHz, $CDCl_3$): δ 7.53, (d, J=2 Hz, 1H), 7.40 (dt, J=8 Hz, J=2 Hz, 2H), 7.22-7.35 (m, 4H), 4.52 (q, J=7 Hz, 2H), 1.45 (t, J=7 Hz, 3H).

Analogously was prepared:
Ethyl-4-(4-chlorophenyl)-5-(2,4-dichlorophenyl)thiazole-2-carboxylate.

Part D; Ethyl-5-(4-chlorophenyl)-4-(2,4-dichlorophenyl) thiazole-2-carboxylate (1.00 gram, 2.42 mmol) is added to 1-aminopiperidine (10 mL) and the resulting stirred mixture is heated at 50° C. for 4 hours. Dichloromethane is added and the resulting solution is washed twice with water, dried over $MgSO_4$, filtered and most of the dichloromethane is removed by evaporation in vacuo. Diisopropyl ether is added and the formed precipitate is removed by filtration. The filtrate is concentrated in vacuo and purified by flash chromatography (ethyl acetate: petroleum ether (40-60)=1:3 (v/v)) to produce 5-(4-chlorophenyl)-4-(2,4-dichlorophenyl)-N-(1-piperidinyl)thiazole-2-carboxamide (330 mg, 29% yield) as a white foam. $^1$H-NMR (400 MHz, $CDCl_3$): δ 7.92 (s, 1H), 7.47 (t, J=2 Hz, 1H), 7.24-7.32 (m, 4H), 7.13 (dt, J=8 Hz, J=2 Hz, 2H), 2.85-2.93 (m, 4H), 1.40-1.82 (m, 6H).

Analogously were prepared:
4-(4-Chlorophenyl)-5-(2,4-dichlorophenyl)-N-(1-piperidinyl)thiazole-2-carboxamide. Melting point: 190-191° C. $^1$H-NMR (400 MHz, $CDCl_3$): δ 8.03 (s, 1H), 7.51 (d, J=2 Hz, 1H), 7.22-7.38 (m, 6H), 2.90-2.97 (m, 4H), 1.75-1.84 (m, 4H), 1.44-1.5 (m, 2H).

5-(4-Chlorophenyl)-N-cycloheptyl-4-(2,4-dichlorophenyl)thiazole-2-carboxamide. Melting point: 159-161° C.

5-(4-Chlorophenyl)-N-cyclopentyl-4-(2,4-dichlorophenyl)thiazole-2-carboxamide. Melting point: 111-113° C.

5-(4-Chlorophenyl)-4-(2,4-dichlorophenyl)-N-(trans-4-hydroxycyclohexyl)thiazole-2-carboxamide. Melting point: 109° C.

5-(4-Chlorophenyl)-4-(2,4-dichlorophenyl)-N-(2-methylcyclohexyl)thiazole-2-carboxamide. Melting point: 134-147° C.

5-(4-Chlorophenyl)-4-(2,4-dichlorophenyl)-N-(4-fluorobenzyl)thiazole-2-carboxamide. Melting point: 142-144° C.

5-(4-Chlorophenyl)-4-(2,4-dichlorophenyl)-N-(trans4-methylcyclohexyl)thiazole-2-carboxamide. Melting point: 165-166° C.

5-(4-Chlorophenyl)-N-(cis-4-methylcyclohexyl)-4-(2,4-dichlorophenyl)thiazole-2-carboxamide. Melting point: 72° C.

EXAMPLE 2

40 Part A; Ethyl-5-(4-chlorophenyl)-4-(2,4-dichlorophenyl)thiazole-2-carboxylate (4.10 gram, 9.93 mmol) is suspended in methanol (75 mL). A solution of KOH (1.98 gram, 30 mmol) in water (75 mL) is added and the resulting mixture is heated at reflux temperature for 2 hours. The resulting yellow solution is allowed to attain room temperature, poured into water and acidified with 1N aqueous HCl to give a white precipitate. This precipitate is collected by filtration and twice washed with water. Drying in vacuo gives 5-(4-chlorophenyl)-4-(2,4-dichlorophenyl)thiazole-2-carboxylic acid as a white solid (2.59 gram, 68% yield). $^1$H-NMR (200 MHz, DMSO-$d_6$): δ 9.25 (s, 1H), 7.65-7.72 (m, 1H), 7.28-7.52 (m, 6H).

Analogously was prepared:
4-(4-Chlorophenyl)-5-(2,4-dichlorophenyl)thiazole-2-carboxylic acid Part B; 5-(4-Chlorophenyl)-4-(2,4-dichlorophenyl)thiazole-2-carboxylic acid (1.00 gram, 2.6 mmol) is suspended in anhydrous acetonitrile (20 mL) under a nitrogen atmosphere at room temperature. Diisopropylethylamine (DIPEA) (1.36 mL, 7.8 mmol), O-benzotriazol-1-yl-N,N,N',N'-tetramethyluronium hexafluorophosphate (HBTU) (1.08 gram, 2.85 mmol) and O-tert-butylhydroxylamine.HCl (0.35 gram, 25.1 mmol) are successively added and the resulting mixture is stirred overnight at room temperature. The resulting mixture is concentrated in vacuo and dichloromethane is added. The resulting solution is successively washed with water and brine, dried over MgSO$_4$, filtered and evaporated in vacuo. Subsequent flash chromatography (ethyl acetate:petroleum ether (40-60)=1:3 (v/v)) gives N-(t-butoxy)-5-(4-chlorophenyl)-4-(2,4-dichlorophenyl)thiazole-2-carboxamide (0.60 gram, 51% yield) as a white foam. $^1$H-NMR (400 MHz, CDCl$_3$): δ 9.20 (s, 1H), 7.47 (t, J=2 Hz, 1H), 7.25-7. (m, 4H), 7.14 (dt, J=8 Hz, J=2 Hz, 2H), 1.36 (s, 9H).

Analogously were prepared:
N-(t-Butoxy)-4-(4-chlorophenyl)-5-(2,4-dichlorophenyl)thiazole-2-carboxamide. $^1$H-NMR (400 MHz, CDCl$_3$): δ 9.23 (s, 1H), 7.52 (d, J=2 Hz, 1H), 7.35 (dt, J=8 Hz, J=2 Hz, 2H) 7.23-7.31 (m, 4H), 1.40 (s, 9H).

5-(4-Chlorophenyl)-4-(2,4-dichlorophenyl)-N-(n-pentyl)thiazole-2-carboxamide $^1$H-NMR (400 MHz, CDCl$_3$): δ 7.46 (s, 1H), 7.21-7.32 (m, 5H), 7.14 (dt, J=8 Hz, J=2 Hz, 2H), 3.42-3.48 (m, 2H), 1.59-1.67 (m, 2H), 1.30-1.40 (m, 4H), 0.90 (t, J=7 Hz, 3H).

5-(4-Chlorophenyl)-N-cyclohexyl-4-(2,4-dichlorophenyl)thiazole-2-carboxamide $^1$H-NMR (400 MHz, CDCl$_3$): δ 7.46 (s, 1H), 7.24-7.35 (m, 4H), 7.05-7.17 (m, 3H), 3.90-4.00 (m, 1H), 1.98-2.07 (m, 2H), 1.72-1.82 (m, 2H), 1.14-1.70 (m, 6H).

EXAMPLE 3

Part A; To 4-bromobenzaldehyde (25 gram, 0.135 mol) is successively added 2,4-dichlorophenylacetic acid (27.7 gram, 0.135 mol), acetic anhydride (100 mL) and triethylamine (19 mL, 0.136 mol) and the resulting mixture is heated at reflux temperature for 90 minutes. The reaction mixture is cooled to 110° C. and water (100 mL) is slowly added. The resulting mixture is allowed to attain room temperature and ethyl acetate is added. The ethyl acetate layer is twice washed with water, dried over MgSO$_4$, filtered and concentrated in vacuo. The resulting oil is crystallised from diisopropyl ether to give 3-(4-bromophenyl)-2-(2,4-dichlorophenyl)acrylic acid as a white solid (26.55 gram, 53% yield).

Part B; 3-(4-Bromophenyl)-2-(2,4-dichlorophenyl)acrylic acid (26.55 gram, 71 mmol) is dissolved in anhydrous toluene (130 mL) and the resulting solution is cooled to 0° C. Triethylamine (7.40 gram, 73 mmol) and diphenylphosphoryl azide (19.8 gram, 72 mmol) are successively added and the resulting mixture Is stirred at 0° C. for 20 minutes and 150 minutes at room temperature. The reaction mixture is poured into water and extracted three times with diethyl ether. The collected organic layers are dried over MgSO$_4$ and the diethyl ether Is removed in vacuo. The resulting toluene layer is slowly added to refluxing toluene (150 mL). t-Butanol is added after 90 minutes and heating at reflux temperature is continued for 1 hour, followed by slow addition of concentrated hydrochloric acid (5 mL). After stirring the resulting solution overnight at 90° C. it is allowed to attain room temperature, washed twice with water, dried over MgSO$_4$, filtered and evaporated in vacuo to give a yellow oil. This oil is crystallised from n-hexane to give 2-(4-bromophenyl)-1-(2,4-dichlorophenyl)ethanone (14.72 gram, 60% yield). Melting point: 69-70° C.

Part C: To a solution of 2-(4-bromophenyl)-1-(2,4-dichlorophenyl)ethanone (5.00 gram, 15 mmol) in benzene (50 mL) is dropwise added bromine (0.75 mL, 15 mmol) and the resulting solution is stirred for 4 hours at room temperature and concentrated in vacuo. Dichloromethane is added and the resulting solution is washed with brine, dried over MgSO$_4$, filtered and concentrated in vacuo to give 2-bromo-2-(4-bromophenyl)-1-(2,4-dichlorophenyl)ethanone as an oil (5.96 gram, 94% yield).

Part D: A solution containing 2-bromo-2-(4-bromophenyl)-1-(2,4-dichlorophenyl)ethanone (5.96 gram, 14 mmol) and ethyl thiooxamate (2.80 gram, 21 mmol) in ethanol (30 mL) is heated at reflux temperature for four hours. After cooling to room temperature the precipitated crystalline material is removed by filtration. The filtrate is concentrated in vacuo and the resulting material (7.56 gram orange oil) is purified by flash chromatography (ethyl acetate/petroleum ether=1/3 (v/v)) and subsequently crystallised from diisopropyl ether to afford ethyl 5-(4-bromophenyl)-4-(2,4-dichlorophenyl)thiazole-2-carboxylate (2.11 gram, 33% yield). Melting point: 129-130° C.

Part E: A stirred mixture containing ethyl 5-(4-bromophenyl)-4-(2,4-dichlorophenyl)thiazole-2-carboxylate (1.00 gram, 2.2 mmol) and 1-aminopiperidine (10 mL) is heated overnight at 50° C. The resulting mixture is allowed to attain room temperature, dichloromethane is added and the resulting solution is twice washed with water, dried over MgSO$_4$, filtered and concentrated in vacuo to give an oil. Flash chromatographic purification of this oil (ethyl acetate/petroleum ether=1/3 (v/v)) gives 5-(4-bromophenyl)-4-(2,4-dichlorophenyl)-N-(1-piperidinyl)thiazole-2-carboxamide (870 mg, 78% yield). Melting point: 171-173° C.

Analogously were prepared:
4-(2,4-Dichlorophenyl)-N-(1-piperidinyl)-5-(4-(trifluoromethyl)phenyl)thiazole-2-carboxamide. Melting point: 181-183° C.

N-Cyclohexyl-4-(2,4-dichlorophenyl)-5-(4-(trifluoromethyl)phenyl)thiazole-2-carboxamide. Melting point: 140-142° C.

4-(2,4-Dichlorophenyl)-N-(exo-bicyclo[2.2.1]hept-2-yl)-5-(4-(trifluoromethyl)phenyl)thiazole-2-carboxamide. Melting point: 184-185° C.

4-(2,4-Dichlorophenyl)-N-(4-morpholinyl)-5-(4-(trifluoromethyl)phenyl)thiazole-2-carboxamide. Melting point: 95° C.

EXAMPLE 4

Part A: Ethyl 5-(4-bromophenyl)-4-(2,4-dichlorophenyl)thiazole-2-carboxylate (1.80 gram, 3.94 mmol) is dissolved in methanol (20 mL) and a solution of KOH (0.65 gram (85%), 9.85 mmol) in water (20 mL) is added. The resulting mixture is heated at reflux temperature for 1 hour, poured into water and acidified with hydrochloric acid (1N solution). The formed precipitated material is collected by filtration and dried in vacuo at room temperature to give a quantitative yield of 5-(4-bromophenyl)-4-(2,4-dichlorophenyl)-thiazole-2-carboxylic acid. Melting point: 94-95° C.

Part B: 5-(4-Bromophenyl)-4-(2,4-dichlorophenyl)thiazole-2-carboxylic acid (0.50 gram, 1.17 mmol) and diisopropylethylamine (DIPEA) (1.02 mL, 5.85 mmol) are dissolved in dichloromethane (5 mL) and cooled to 0° C. 7-Aza-1-hydroxybenzotriazole (HOAt) (0.11 gram, 0.81 mmol) and 2-chloro-1,3-dimethylimidazolinium hexafluorophosphate (CIP) (0.50 gram, 1.76 mmol) are added, followed by addition of n-pentylamine (0.15 gram, 1.76 mmol) and the resulting mixture is stirred at room temperature overnight. Flash chromatographic purification (dichloromethane) gives 5-(4-bromophenyl)-4-(2,4-dichlorophenyl)-N-(n-pentyl)thiazole-2-carboxamide as an amorphous solid (0.28 gram, 48% yield).

Analogously were prepared:

5-(4-Bromophenyl)-4-(2,4-dichlorophenyl)-N-(hexahydro(1H)azepin-1-yl)thiazole-2-carboxamide. Melting point: 206-207° C.

5-(4-Chlorophenyl)-4-(2,4-dichlorophenyl)-N-(morpholin-4-yl)thiazole-2-carboxamide. Amorphous solid.

5-(4-Chlorophenyl)-4-(2,4-dichlorophenyl)-N-(pyrrolidin-1-yl)thiazole-2-carboxamide. Melting point: 179-181° C.

EXAMPLE 5

Part A: To a solution of 5-(4-chlorophenyl)-4-(2,4-dichlorophenyl)thiazole-2-carboxylic acid (0.50 gram, 1.30 mmol) in dichloromethane (10 mL) is successively added 1-aminohexahydro(1H)azepine (0.15 gram, 1.30 mmol), 7-aza-1-hydroxybenzotriazole (0.18 gram, 1.30 mmol), 7-azabenzotriazol-1-yloxytris(pyrrolidino)phosphonium hexafluorophosphate (PyAOP) (0.68 gram, 1.30 mmol) and diisopropylethylamine (0.34 mL, 1.95 mmol) and the resulting solution is stirred for 1 hour at room temperature. Concentration In vacuo gives a crude oil (2.01 gram) which is purified by flash chromatography (ethyl acetate/petroleum ether=1/3 (v/v)) to give 5-(4-chlorophenyl)-4-(2,4-dichlorophenyl)-N-(hexahydro(1H)azepin-1-yl)thiazole-2-carboxamide (0.350 gram, 56% yield). Melting point: 185-186° C. (after recrystallisation from diisopropyl ether).

Analogously were prepared:

5-(4-Chlorophenyl)-4-(2,4-dichlorophenyl)-N-(hexahydrocyclopenta-[c]pyrrol-2(1H)-yl)thiazole-2-carboxamide. Melting point: 173-174° C.

N-Benzyl-5-(4-chlorophenyl)-4-(2,4-dichlorophenyl)-N-methyl-thiazole-2-carboxamide. Melting point: 141-144° C.

5-(4-Chlorophenyl)-4-(2,4-dichlorophenyl)-N-(4-(trifluoromethyl)benzyl)thiazole-2-carboxamide. Melting point: 174-176° C.

5-(4-Chlorophenyl)-4-(2,4-dichlorophenyl)-N-(exo-bicyclo[2.2.1]hept-2-yl)thiazole-2-carboxamide. Melting point: 194-195° C.

5-(4-Chlorophenyl)-4-(2,4-dichlorophenyl)-N-(endo-bicyclo[2.2.1]hept-2-yl)thiazole-2-carboxamide. Melting point: 181-183° C.

4-(2,5-Dichlorophenyl)-N-(exo-bicyclo[2.2.1]hept-2-yl)-5-(phenyl)thiazole-2-carboxamide. Melting point: 170° C.

N-(Cyclohexyl)-4-(2,5-dichlorophenyl)-5-(phenyl)thiazole-2-carboxamide. Melting point: 75° C.

5-(4-Chlorophenyl)-4-(2,4-dichlorophenyl)-N-(tetrahydro-2H-pyran-2-yloxy)thiazole-2-carboxamide. Melting point: 85° C.

5-(4-Chlorophenyl)-4-(2,4-dichlorophenyl)-N-(5,5,5-trifluoropentyl)thiazole-2-carboxamide. $^1$H-NMR (400 MHz, CDCl$_3$): δ 7.47 (br s, 1H), 7.24-7.31 (m, 5H), 7.14 (dt, J=8 Hz, J=2 Hz, 2H), 3.49 (q, J=7 Hz, 2H), 2.07-2.20 (m, 2H), 1.62-1.77 (m, 4H).

5-(4-Chlorophenyl)-4-(2,4-dichlorophenyl)-N-(2-fluoroethyl)thiazole-2-carboxamide. Amorphous solid. $^1$H-NMR (400 MHz, CDCl$_3$): δ 7.52-7.58 (m, 1H), 7.47 (br s, 1H), 7.24-7.32 (m, 4H), 7.14 (dt, J=8 Hz, J=2 Hz, 2H), 4.61 (dt, J=47 Hz, J=5 Hz, 2H), 3.72-3.84 (m, 2H).

5-(4-Chlorophenyl)-4-(2,4-dichlorophenyl)-N-(5-fluoropentyl)thiazole-2-carboxamide. $^1$H-NMR (400 MHz, CDCl$_3$): δ 7.47 (br s, 1H), 7.24-7.30 (m, 5H), 7.14 (dt, J=8 Hz, J=2 Hz, 2H), 4.45 (dt, J=47 Hz, J=6 Hz, 2H), 3.45-3.51 (m, 2H), 1.64-1.82 (m, 4H), 1.48-1.56 (m, 2H).

4-(2,5-Dichlorophenyl)-N-(4-morpholinyl)-5-(phenyl)thiazole-2-carboxamide. Melting point: 155-157° C.

EXAMPLE 6

5-Ethyl-5-(4-chlorophenyl)-4-(2,4-dichlorophenyl)thiazole-2-carboxylate (1.65 gram, 4.0 mmol) is dissolved in anhydrous THF (25 mL) and aniline (0.37 mL, 4.0 mmol) is added. The resulting solution is cooled to 0° C. and sodium hexamethyidisilazide (4.4 mL of a 1M solution in THF) is added. The reaction mixture is stirred for 2 hours. Water is added and the mixture is extracted twice with ethyl acetate. The combined organic layer is washed with brine, dried over MgSO$_4$, filtered and concentrated in vacuo. The residue is crystallised from diisopropyl ether to give 5-(4-chlorophenyl)-4-(2,4-dichlorophenyl)-N-phenyl-thiazole-2-carboxamide (1.42 g, 77% yield). Melting point: 167-168° C.

EXAMPLE 7

Part A: Gaseous NH$_3$ is led through a stirred solution of ethyl 5-(4-chlorophenyl)-4-(2,4-dichlorophenyl)thiazole-2-carboxylate (1.65 gram, 4.0 mmol) in methanol (25 mL) at room temperature. A small piece of sodium metal is added. After stirring the resulting mixture for three hours the precipitate is collected by filtration, washed with a small portion of methanol and dried to give 5-(4-chlorophenyl)-4-(2,4-dichlorophenyl)thiazole-2-carboxamide (1.16 gram, 76% yield), melting point 195-198° C. $^1$H-NMR (200 MHz, CDCl$_3$): δ 7.48 (br s, 1H), 7.22-7.35 (m, 4H), 7.05-7.20 (m, 3H) 5.55-5.65 (M, 1H).

Part B: To a cooled (0° C.) stirred solution of 5-(4-chlorophenyl)-4-(2,4-dichlorophenyl)thiazole-2-carboxamide (1.16 gram, 3.02 mmol) in anhydrous DMF (20 mL) is added NaH (0.13 gram of a 60% dispersion) in a nitrogen atmosphere. The resulting mixture is stirred for 1 hour and excess 4,4,4-trifluoro-1-bromobutane (0.7 mL) is added. The resulting solution is stirred at room temperature for 1 hour, poured onto ice/water and extracted twice with diethyl ether. The collected diethyl ether layers are twice washed with water, dried over Na$_2$SO$_4$, filtered and concentrated in vacuo. The residue is further purified by column chromatography (silica gel; eluant: dichloromethane) to give 5-(4-chlorophenyl)-4-(2,4-dichlorophenyl)-N-(4,4,4-trifluorobutyl)thiazole-2-carboxamide. Melting point: 99-101° C.

The invention claimed is:

1. A compound of formula (I)

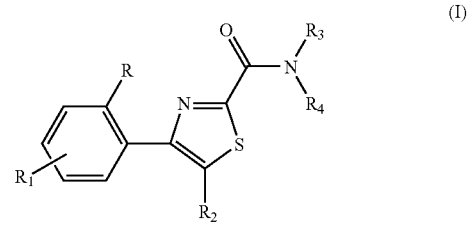

wherein

R is chosen from substituent X,
  wherein X is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkoxycarbonyl, trifluoromethylsulfonyl, sulfamoyl, branched or unbranched alkyl-($C_{1-3}$)-sulfonyl, carboxyl, cyano, carbamoyl, branched or unbranched dialkyl-($C_{1-3}$)-aminosulfonyl, branched or unbranched monoalkyl-($C_{1-3}$)-aminosulfonyl, and acetyl groups;

$R_1$ is chosen from a hydrogen atom and 1 to 4 substituents X,
  wherein X is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, mononoalkyl-($C_{1-2}$)-amido, dialkyl-($C_{1-2}$)-amido, branched or unbranched ($C_{1-3}$)-alkoxycarbonyl, trifluoromethylsulfonyl, sulfamoyl, branched or unbranched alkyl-($C_{1-3}$)-sulfonyl, carboxyl, cyano, carbamoyl, branched or unbranched dialkyl-($C_{1-3}$)-aminosulfonyl, branched or unbranched monoalkyl-($C_{1-3}$)-aminosulfonyl, and acetyl groups;

$R_2$ is chosen from:
  a naphthyl group; and
  phenyl, thienyl, pyridyl, and pyrimidinyl groups,
    wherein the phenyl, thienyl, pyridyl, and pyrimidinyl groups may optionally be substituted with 1 to 4 substituents X,
    wherein X is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkoxycarbonyl, trifluoromethylsulfonyl, sulfamoyl, branched or unbranched alkyl-($C_{1-3}$)-sulfonyl, carboxyl, cyano, carbamoyl, branched or unbranched dialkyl-($C_{1-3}$)-aminosulfonyl, branched or unbranched monoalkyl-($C_{1-3}$)-aminosulfonyl, and acetyl groups;

$R_3$ is chosen from:
  a hydrogen atom, a branched or unbranched ($C_{1-10}$)-alkyl or cycloalkyl-alkyl group, a pyridyl group, and a thienyl group; and
  a phenyl group, a benzyl group, and a phenethyl group,
    wherein the aromatic rings of the phenyl, benzyl and phenethyl groups may optionally be substituted with 1 to 5 substituents Z, which can be the same or different,
    wherein Z is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkylsulfonyl, dimethylsulfamido, branched or unbranched ($C_{1-3}$)-alkoxycarbonyl, carboxyl, trifluoromethylsulfonyl, cyano, carbamoyl, sulfamoyl, and acetyl groups; and $R_4$ is chosen from:
  branched or unbranched ($C_{1-10}$)-alkyl or cycloalkyl-alkyl groups, branched or unbranched ($C_{1-10}$)-alkoxy, ($C_{3-8}$)-cycloalkyl, ($C_{5-10}$)-bicycloalkyl, ($C_{6-10}$)-tricycloalkyl, branched or unbranched ($C_{3-10}$)-alkenyl, and ($C_{5-8}$)-cycloalkenyl groups,
    wherein the branched or unbranched ($C_{1-10}$)-alkyl or cycloalkyl-alkyl groups, branched or unbranched ($C_{1-10}$)-alkoxy, ($C_{3-8}$)-cycloalkyl, ($C_{5-10}$)-bicycloalkyl, ($C_{6-10}$)-tricycloalkyl, branched or unbranched ($C_{3-10}$)-alkenyl, ($C_{5-8}$)-cycloalkenyl groups may optionally contain at least one heteroatom chosen from oxygen, nitrogen, and sulphur, and may optionally be substituted with a substituent chosen from a hydroxy group, 1 to 3 methyl groups, an ethyl group, and 1 to 3 fluorine atoms;
  phenyl, benzyl, and phenethyl groups,
    wherein the aromatic rings of the phenyl, benzyl and phenethyl groups may optionally be substituted with 1 to 5 substituents Z,
    wherein Z is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl($C_{1-2}$)-amido, dialkyl-($C_{1-2}$)-amido, branched or unbranched ($C_{1-3}$)-alkylsulfonyl, dimethylsulfamido, branched or unbranched ($C_{1-3}$)-alkoxycarbonyl, carboxyl, trifluoromethylsulfonyl, cyano, carbamoyl, sulfamoyl, and acetyl groups;
  pyridyl and thienyl groups; and
  $NR_5R_6$ groups,
    wherein $R_5$ and $R_6$, together with the nitrogen atom to which they are attached, form a saturated or unsaturated, monocyclic or bicyclic, heterocyclic group having 4 to 10 ring atoms,
    wherein the heterocyclic group contains at least one heteroatom chosen from oxygen, nitrogen, and sulphur, and may optionally be substituted with a substituent chosen from a branched or unbranched ($C_{1-3}$)-alkyl group, a hydroxy group, a trifluoromethyl group, and a fluorine atom; or $R_3$ and $R_4$, together with the nitrogen atom to which they are attached, form a saturated or unsaturated, monocyclic or bicyclic, heterocyclic group having 4 to 10 ring atoms,
  wherein the heterocyclic group contains at least one heteroatom chosen from oxygen, nitrogen, and sulphur, and may optionally be substituted with a substituent chosen from a branched or unbranched ($C_{1-3}$)-alkyl group, a hydroxy group, a trifluoromethyl group, and a fluorine atom;

or stereoisomers and salts thereof.

2. A compound of formula (I)

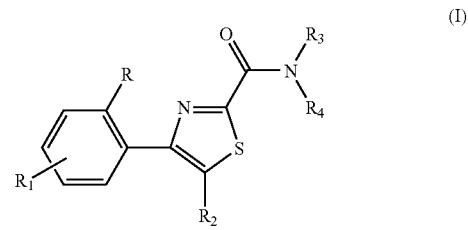

13 wherein

R is substituent Y,
  wherein Y is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkoxycarbonyl, carboxyl, cyano, carbamoyl, and acetyl groups;

$R_1$ is chosen from hydrogen and at least one substituent Y,
  wherein Y is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkoxycarbonyl, carboxyl, cyano, carbamoyl, and acetyl groups;

$R_2$ is chosen from:
  a naphthyl group; and
  phenyl, thienyl, pyridyl, and pyrimidinyl groups,
    wherein the phenyl, thienyl, pyridyl, and pyrimidinyl groups may optionally be substituted with at least one substituent Y,
    wherein Y is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkoxycarbonyl, carboxyl, cyano, carbamoyl, and acetyl groups;

$R_3$ is hydrogen; and $R_4$ is chosen from:
  branched or unbranched ($C_{1-10}$)-alkyl or alkyl-cycloalkyl, branched or unbranched ($C_{1-10}$)-alkoxy, ($C_{3-8}$)-cycloalkyl, ($C_{5-10}$)-bicycloalkyl, ($C_{1-10}$)-tricycloalkyl, branched or unbranched ($C_{3-10}$)-alkenyl, and ($C_{5-8}$)-cycloalkenyl groups,
    wherein the branched or unbranched ($C_{1-10}$)-alkyl or alkyl-cycloalkyl, branched or unbranched ($C_{1-10}$)-alkoxy, ($C_{3-8}$)-cycloalkyl, ($C_{5-10}$)-bicycloalkyl, ($C_{6-10}$)-tricycloalkyl, branched or unbranched ($C_{3-10}$)-alkenyl, and ($C_{5-8}$)-cycloalkenyl groups may optionally contain at least one heteroatom chosen from oxygen, nitrogen, and sulphur, and may optionally be substituted with a substituent chosen from a hydroxy group, 1 to 3 methyl groups, an ethyl group, and 1 to 3 fluorine atoms;
  benzyl and phenethyl groups,
    wherein the aromatic rings of the benzyl and phenethyl groups may optionally be substituted with at least one substituent Z, which can be the same or different,
    wherein Z is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkylsulfonyl, dimethylsulfamido, branched or unbranched ($C_{1-3}$)-alkoxycarbonyl, carboxyl, trifluoromethylsulfonyl, cyano, carbamoyl, sulfamoyl, and acetyl groups;
  pyridyl and thienyl groups; and
  $NR_5R_6$ groups,
    wherein $R_5$ and $R_6$, together with the nitrogen atom to which they are attached, form a saturated or unsaturated, monocyclic or bicyclic, heterocyclic group having 4 to 10 ring atoms,

14 wherein the heterocyclic group contains at least one heteroatom chosen from oxygen, nitrogen, and sulphur, and may optionally be substituted with a substituent chosen from branched or unbranched ($C_{1-3}$)-alkyl groups, a hydroxy group, a trifluoromethyl group, and a fluorine atom;
or stereoisomers and salts thereof.

3. A compound of formula (I)

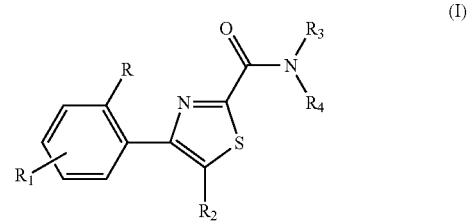

wherein

R is substituent Y,
  wherein Y is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkoxycarbonyl, carboxyl, cyano, carbamoyl, and acetyl groups;

$R_1$ is chosen from at least one substituent Y,
  wherein Y is chosen from branched or unbranched ($C_{1-3}$)-alkyl or aikoxy, hydroxy, halogen, trifluoromethyl, trifluoromethylthio, trifluoromethoxy, nitro, amino, monoalkyl-($C_{1-2}$)-amino or dialkyl-($C_{1-2}$)-amino, monoalkyl-($C_{1-2}$)-amido or dialkyl-($C_{1-2}$)-amido, branched or unbranched ($C_{1-3}$)-alkoxycarbonyl, carboxyl, cyano, carbamoyl, and acetyl groups;

$R_2$ is chosen from:
  a naphthyl group; and
  phenyl, thienyl, pyridyl and pyrimidinyl groups,
    wherein the phenyl, thienyl, pyridyl and pyrimidinyl groups may optionally be substituted with one or more substituents Y,
    wherein Y is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkoxycarbonyl, carboxyl, cyano, carbamoyl, and acetyl groups;

$R_3$ is hydrogen; and $R_4$ is chosen from:
  branched or unbranched ($C_{1-10}$)-alkyl or alkyl-cycloalkyl, branched or unbranched ($C_{1-10}$)-alkoxy, ($C_{3-8}$)-cycloalkyl, ($C_{5-10}$)-bicycloalkyl, ($C_{6-10}$)-tricycloalkyl, branched or unbranched ($C_{3-10}$)-alkenyl, and ($C_{5-8}$)-cycloalkenyl groups,
    wherein the branched or unbranched ($C_{1-10}$)-alkyl or alkyl-cycloalkyl, branched or unbranched ($C_{1-10}$)-alkoxy, ($C_{3-8}$)-cycloalkyl, ($C_{5-10}$)-bicycloalkyl, ($C_{6-10}$)-tricycloalkyl, branched or unbranched ($C_{3-10}$)-alkenyl, and ($C_{5-8}$)-cycloalkenyl groups may optionally contain at least one heteroatom chosen from oxygen, nitrogen, and sulphur, and may optionally be substituted with a substituent chosen from a hydroxy group, 1 to 3 methyl groups, an ethyl group, and 1 to 3 fluorine atoms;

benzyl and phenethyl groups,
wherein the aromatic rings of the benzyl and phenethyl groups may optionally be substituted with at least one substituent Z, which can be the same or different,
wherein Z is chosen from branched or unbranched $(C_{1-3})$-alkyl or alkoxy, hydroxy, halogen, trifluoromethyl, trifluoromethylthio, trifluoromethoxy, nitro, amino, monoalkyl-$(C_{1-2})$-amino, dialkyl-$(C_{1-2})$-amino, monoalkyl-$(C_{1-2})$-amido, dialkyl-$(C_{1-2})$-amido, branched or unbranched $(C_{1-3})$-alkylsulfonyl, dimethylsulfamido, branched or unbranched $(C_{1-3})$-alkoxycarbonyl, carboxyl, trifluoromethylsulfonyl, cyano, carbamoyl, sulfamoyl, and acetyl groups;

pyridyl and thienyl groups;

$NR_5R_6$ groups,
wherein $R_5$ and $R_6$, together with the nitrogen atom to which they are attached, form a saturated or unsaturated, monocyclic or bicyclic, heterocyclic group having 4 to 10 ring atoms,
wherein the heterocyclic group contains at least one heteroatom chosen from oxygen, nitrogen, and sulphur, and may optionally be substituted with a substituent chosen from a branched or unbranched $(C_{1-3})$-alkyl group, a hydroxy group, a trifluoromethyl group, and a fluorine atom;

or stereoisomers and salts thereof.

4. A compound of formula (I)

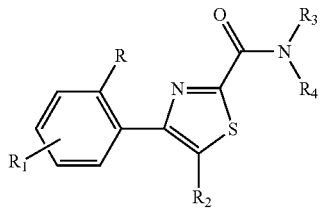

(I)

wherein
R is a halogen atom;
$R_1$ is chosen from at least one substituent Y,
wherein Y is chosen from branched or unbranched $(C_{1-3})$-alkyl or alkoxy, hydroxy, halogen, trifluoromethyl, trifluoromethylthio, trifluoromethoxy, nitro, amino, monoalkyl-$(C_{1-2})$-amino, dialkyl-$(C_{1-2})$-amino, monoalkyl-$(C_{1-2})$-amido, dialkyl-$(C_{1-2})$-amido, branched or unbranched $(C_{1-3})$-alkoxycarbonyl, carboxyl, cyano, carbamoyl, and acetyl groups;

$R_2$ is chosen from:
a naphthyl group; and
phenyl, thienyl, pyridyl and pyrimidinyl groups,
wherein the phenyl, thienyl, pyridyl and pyrimidinyl groups may optionally be substituted with at least one substituent Y,
wherein Y is chosen from branched or unbranched $(C_{1-3})$-alkyl or alkoxy, hydroxy, halogen, trifluoromethyl, trifluoromethylthio, trifluoromethoxy, nitro, amino, monoalkyl-$(C_{1-2})$-amino, dialkyl-$(C_{1-2})$-amino, monoalkyl-$(C_{1-2})$-amido, dialkyl-$(C_{1-2})$-amido, branched or unbranched $(C_{1-3})$-alkoxycarbonyl, carboxyl, cyano, carbamoyl, and acetyl groups;

$R_3$ is hydrogen; and
$R_4$ is chosen from:
branched or unbranched $(C_{1-10})$-alkyl or alkyl-cycloalkyl, branched or unbranched $(C_{1-10})$-alkoxy, $(C_{3-8})$-cycloalkyl, $(C_{5-10})$-bicycloalkyl, $(C_{6-10})$-tricycloalkyl, branched or unbranched $(C_{3-10})$-alkenyl, and $(C_{5-8})$-cycloalkenyl groups,
wherein the branched or unbranched $(C_{1-10})$-alkyl or alkyl-cycloalkyl, branched or unbranched $(C_{1-10})$-alkoxy, $(C_{3-8})$-cycloalkyl, $(C_{5-10})$-bicycloalkyl, $(C_{6-10})$-tricycloalkyl, branched or unbranched $(C_{3-10})$-alkenyl, and $(C_{5-8})$-cycloalkenyl groups may optionally contain at least one heteroatom chosen from oxygen, nitrogen, and sulphur, and may optionally be substituted with a substituent chosen from a hydroxy group, 1 to 3 methyl groups, an ethyl group, and 1 to 3 fluorine atoms;

benzyl and phenethyl groups,
wherein the aromatic rings of the benzyl and phenethyl groups may optionally be substituted with at least one substituent Z, which can be the same or different,
wherein Z is chosen from branched or unbranched $(C_{1-3})$-alkyl or alkoxy, hydroxy, halogen, trifluoromethyl, trifluoromethylthio, trifluoromethoxy, nitro, amino, monoalkyl-$(C_{1-2})$-amino, dialkyl-$(C_{1-2})$-amino, monoalkyl-$(C_{1-2})$-amido, dialkyl-$(C_{1-2})$-amido, branched or unbranched $(C_{1-3})$-alkylsulfonyl, dimethylsulfamido, branched or unbranched $(C_{1-3})$-alkoxycarbonyl carboxyl, trifluoromethylsulfonyl, cyano, carbamoyl, sulfamoyl and acetyl groups;

pyridyl and thienyl groups; and $NR_5R_6$ groups,
wherein $R_5$ and $R_6$ together with the nitrogen atom to which they are attached form a saturated or unsaturated, monocyclic or bicyclic, heterocyclic group having 4 to 10 ring atoms,
wherein the heterocyclic group contains at least one heteroatom chosen from oxygen, nitrogen, and sulphur, and may optionally be substituted with a substituent chosen from a branched or unbranched $(C_{1-3})$-alkyl group, a hydroxy group, a trifluoromethyl group, and a fluorine atom;

or stereoisomers and salts thereof.

5. A compound of formula (I)

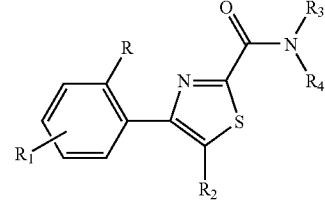

(I)

wherein
R is a halogen atom
$R_1$ is chosen from at least one substituent Y,
wherein Y is chosen from branched or unbranched $(C_{1-3})$-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkoxycarbonyl, carboxyl, cyano, carbamoyl, and acetyl groups;

$R_2$ is chosen from:
  a naphthyl group; and
  phenyl, thienyl, pyridyl, and pyrimidinyl groups,
    wherein the phenyl, thienyl, pyridyl, and pyrimidinyl groups may optionally be substituted with at least one substituent Y,
      wherein Y is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkoxycarbonyl, carboxyl, cyano, carbamoyl and acetyl groups;

$R_3$ is hydrogen; and $R_4$ is chosen from $NR_5R_6$ groups,
  wherein $R_5$ and $R_6$, together with the nitrogen atom to which they are attached, form a saturated or unsaturated, monocyclic or bicyclic, heterocyclic group having 4 to 10 ring atoms,
  wherein the heterocyclic group contains at least one heteroatom chosen from oxygen, nitrogen, and sulphur, and may optionally be substituted with a substituent chosen from a branched or unbranched ($C_{1-3}$)-alkyl group, a hydroxy group, a trifluoromethyl group, and a fluorine atom;
or stereoisomers and salts thereof.

6. A compound of formula (I)

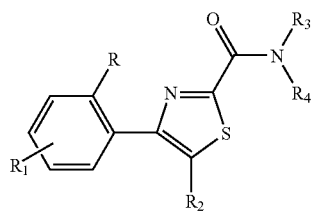

wherein
R is a halogen atom;
$R_1$ is chosen from at least one halogen atom;
$R_2$ is chosen from:
  a naphthyl group; and
  phenyl, thienyl, pyridyl or pyrimidinyl groups,
    wherein the phenyl, thienyl, pyridyl and pyrimidinyl groups may optionally be substituted with at least one substituent Y,
      wherein Y is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkoxycarbonyl, carboxyl, cyano, carbamoyl, and acetyl groups;

$R_3$ is hydrogen; and $R_4$ is chosen from $NR_5R_6$ groups,
  wherein $R_5$ and $R_6$, together with the nitrogen atom to which they are attached, form a saturated or unsaturated, monocyclic or bicyclic, heterocyclic group having 4 to 10 ring atoms,
  wherein the heterocyclic group contains at least one heteroatom chosen from oxygen, nitrogen, and sulphur, and may optionally be substituted with a substituent chosen from a branched or unbranched ($C_{1-3}$)-alkyl group, a hydroxy group, a trifluoromethyl group, and a fluorine atom;
or stereoisomers and salts thereof.

7. A method of treating at least one disorder involving $CB_1$ cannabinoid neurotransmission or neurological disorders, wherein said disorder is chosen from anxiety, depression, appetite disorders, obesity, and pain, comprising:
  administering to a patient in need of treatment an effective amount of at least one compound of formula (I):

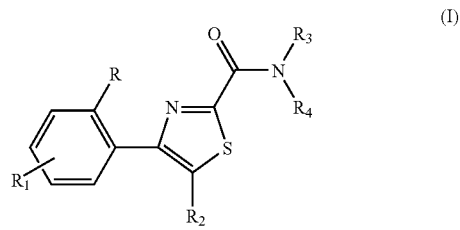

wherein
R is chosen from a hydrogen atom and a substituent X,
  wherein X is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkoxycarbonyl, trifluoromethylsulfonyl, sulfamoyl, branched or unbranched alkyl-($C_{1-3}$)-sulfonyl, carboxyl, cyano, carbamoyl, branched or unbranched dialkyl-($C_{1-3}$)-aminosulfonyl, branched or unbranched monoalkyl-($C_{1-3}$)-aminosulfonyl, and acetyl groups;

$R_1$ is chosen from a hydrogen atom and 1 to 4 substituents X,
  wherein X is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkoxycarbonyl, trifluoromethylsulfonyl, sulfamoyl, branched or unbranched alkyl-($C_{1-3}$)-sulfonyl, carboxyl, cyano, carbamoyl, branched or unbranched dialkyl-($C_{1-3}$)-aminosulfonyl, branched or unbranched monoalkyl-($C_{1-3}$)-aminosulfonyl, and acetyl groups;

$R_2$ is chosen from:
  a naphthyl group; and
  phenyl, thienyl, pyridyl and pyrimidinyl groups,
    wherein the phenyl, thienyl, pyridyl and pyrimidinyl groups may optionally be substituted with 1 to 4 substituents X,
      wherein X is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkoxycarbonyl, trifluoromethylsulfonyl, sulfamoyl, branched or unbranched alkyl-($C_{1-3}$)- sulfonyl, carboxyl, cyano, carbamoyl, branched or unbranched dialkyl-$(C_{1-3})$-aminosulfonyl, branched or unbranched monoalkyl-$(C_{1-3})$-aminosulfonyl, and acetyl groups;

$R_3$ is chosen from:
a hydrogen atom, a branched or unbranched $(C_{1-10})$-alkyl or cycloalkyl-alkyl group, a pyridyl group, and a thienyl group; and
phenyl, benzyl and phenethyl groups,
wherein the aromatic rings of the phenyl, benzyl and phenethyl groups may optionally be substituted with 1 to 5 substituents Z, which can be the same or different,
wherein Z is chosen from branched or unbranched $(C_{1-3})$-alkyl or alkoxy, hydroxy, halogen, trifluoromethyl, trifluoromethylthio, trifluoromethoxy, nitro, amino, monoalkyl-$(C_{1-2})$-amino, dialkyl-$(C_{1-2})$-amino, monoalkyl-$(C_{1-2})$-amido, dialkyl-$(C_{1-2})$-amido, branched or unbranched $(C_{1-3})$-alkylsulfonyl, dimethylsulfamido, branched or unbranched $(C_{1-3})$-alkoxycarbonyl, carboxyl, trifluoromethylsulfonyl, cyano, carbamoyl, sulfamoyl, and acetyl groups; and $R_4$ is chosen from:
branched or unbranched $(C_{1-10})$-alkyl or cycloalkyl-alkyl group, branched or unbranched $(C_{1-10})$-alkoxy, $(C_{3-8})$-cycloalkyl, $(C_{5-10})$-bicycloalkyl, $(C_{6-10})$-tricycloalkyl, branched or unbranched $(C_{3-10})$-alkenyl, and $(C_{5-8})$-cycloalkenyl groups,
wherein the branched or unbranched $(C_{1-10})$-alkyl or cycloalkyl-alkyl group, branched or unbranched $(C_{1-10})$-alkoxy, $(C_{3-8})$-cycloalkyl, $(C_{5-10})$-bicycloalkyl, $(C_{6-10})$-tricycloalkyl, branched or unbranched $(C_{3-10})$-alkenyl, and $(C_{5-8})$-cycloalkenyl groups may optionally contain at least one heteroatom chosen from oxygen, nitrogen, and sulphur, and may optionally be substituted with a substituent chosen a hydroxy group, 1 to 3 methyl groups, an ethyl group, and 1 to 3 fluorine atoms;
phenyl, benzyl, and phenethyl groups,
wherein the aromatic rings of the phenyl, benzyl, and phenethyl groups may optionally be substituted with 1 to 5 substituents 7,
wherein Z is chosen from branched or unbranched $(C_{1-3})$-alkyl or alkoxy, hydroxy, halogen, trifluoromethyl, trifluoromethylthio, trifluoromethoxy, nitro, amino, monoalkyl-$(C_{1-2})$-amino, dialkyl-$(C_{1-2})$-amino, monoalkyl-$(C_{1-2})$-amido, dialkyl-$(C_{1-2})$-amido, branched or unbranched $(C_{1-3})$-alkylsulfonyl, dimethylsulfamido, branched or unbranched $(C_{1-3})$-alkoxycarbonyl, carboxyl, trifluoromethylsulfonyl, cyano, carbamoyl, sulfamoyl, and acetyl groups;
pyridyl and thienyl groups; and
$NR_5R_6$ groups,
wherein $R_5$ and $R_6$, together with the nitrogen atom to which they are attached, form a saturated or unsaturated, monocyclic or bicyclic, heterocyclic group having 4 to 10 ring atoms,
wherein the heterocyclic group contains at least one heteroatom chosen from oxygen, nitrogen, and sulphur, and may optionally be substituted with a substituent chosen from a branched or unbranched $(C_{1-3})$-alkyl group, a hydroxy group, a trifluoromethyl group, and a fluorine atom; or $R_3$ and $R_4$, together with the nitrogen atom to which they are attached, form a saturated or unsaturated, monocyclic or bicyclic, heterocyclic group having 4 to 10 ring atoms,
wherein the heterocyclic group contains at least one heteroatom chosen from oxygen, nitrogen, and sulphur, and may optionally be substituted with a substituent chosen from a branched or unbranched $(C_{1-3})$-alkyl group, a hydroxy group; a trifluoromethyl group, and a fluoro atom;
or stereoisomers, and salts thereof.

8. A pharmaceutical composition comprising at least one active component chosen from a compound of formula (I),

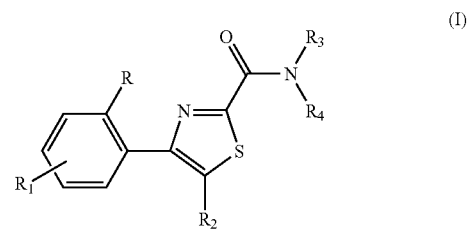

wherein
R is chosen from substituent X,
wherein X is chosen from branched or unbranched $(C_{1-3})$-alkyl or alkoxy, hydroxy, halogen, trifluoromethyl, trifluoromethylthio, trifluoromethoxy, nitro, amino, mono-$(C_{1-2})$-amino, dialkyl-$(C_{1-2})$-amino, monoalkyl-$(C_{1-2})$amido, dialkyl-$(C_{1-2})$-amido, branched or unbranched $(C_{1-3})$-alkoxycarbonyl, trifluoromethylsulfonyl, sulfamoyl, branched or unbranched alkyl-$(C_{1-3})$-sulfonyl, carboxyl, cyano, carbamoyl, branched or unbranched dialkyl-$(C_{1-3})$-aminosulfonyl, branched or unbranched monoalkyl-$(C_{1-3})$-aminosulfonyl, and acetyl groups;

$R_1$ is chosen from a hydrogen atom and 1 to 4 substituents X,
wherein X is chosen from branched or unbranched $(C_{1-3})$-alkyl or alkoxy, hydroxy, halogen, trifluoromethyl, trifluoromethylthio, trifluoromethoxy, nitro, amino, monoalkyl-$(C_{1-2})$-amino, dialkyl-$(C_{1-2})$-amino, monoalkyl-$(C_{1-2})$-amido, dialkyl-$(C_{1-2})$-amido, branched or unbranched $(C_{1-3})$-alkoxycarbonyl, trifluoromethylsulfonyl, sulfamoyl, branched or unbranched alkyl-$(C_{1-3})$-sulfonyl, carboxyl, cyano, carbamoyl, branched or unbranched dialkyl-$(C_{1-3})$-aminosulfonyl, branched or unbranched monoalkyl-$(C_{1-3})$-aminosulfonyl and acetyl groups;

$R_2$ is chosen from:
a naphthyl group; and
phenyl, thienyl, pyridyl, and pyrimidinyl groups,
wherein the phenyl, thienyl, pyridyl, and pyrimidinyl groups may optionally be substituted with 1 to 4 substituents X,
wherein X is chosen from branched or unbranched $(C_{1-3})$-alkyl or alkoxy, hydroxy, halogen, trifluoromethyl, trifluoromethylthio, trifluoromethoxy, nitro, amino, monoalkyl-$(C_{1-2})$-amino, dialkyl-$(C_{1-2})$-amino, monoalkyl-$(C_{1-2})$-amido, dialkyl-$(C_{1-2})$-amido, branched or unbranched $(C_{1-3})$-alkoxycarbonyl, trifluoromethylsulfonyl, sulfamoyl, branched or unbranched alkyl-$(C_{1-3})$-sulfonyl, carboxyl, cyano, carbamoyl, branched or unbranched dialkyl-($C_{1-3}$)-aminosulfonyl, branched or unbranched monoalkyl-($C_{1-3}$)-aminosulfonyl, and acetyl groups;

$R_3$ is chosen from:
a hydrogen atom, a branched or unbranched ($C_{1-10}$)-alkyl or cycloalkyl-alkyl group, a pyridyl group, and a thienyl group; and
phenyl, benzyl, and phenethyl groups,
wherein the aromatic rings of the phenyl, benzyl, and phenethyl groups may optionally be substituted with 1 to 5 substituents Z, which can be the same or different,
wherein Z is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkylsulfonyl, dimethylsulfamido, branched or unbranched ($C_{1-3}$)-alkoxycarbonyl, carboxyl, trifluoromethylsulfonyl, cyano, carbamoyl, sulfamoyl, and acetyl groups; and $R_4$ is chosen from:
branched or unbranched ($C_{1-10}$)-alkyl or cycloalkyl-alkyl groups, branched or unbranched ($C_{1-10}$)-alkoxy, ($C_{3-8}$)-cycloalkyl, ($C_{5-10}$)-bicycloalkyl, ($C_{6-10}$)-tricycloalkyl, branched or unbranched ($C_{3-10}$)-alkenyl, and ($C_{5-8}$)-cycloalkenyl,
wherein the branched or unbranched ($C_{1-10}$)-alkyl or cycloalkyl-alkyl groups, branched or unbranched ($C_{1-10}$)-alkoxy, ($C_{3-8}$)-cycloalkyl, ($C_{5-10}$)-bicycloalkyl, ($C_{6-10}$)-tricycloalkyl, branched or unbranched ($C_{3-10}$)-alkenyl, ($C_{5-8}$)-cycloalkenyl groups may optionally contain at least one heteroatom chosen from oxygen, nitrogen, and sulphur, and may optionally be substituted with a substituent chosen from a hydroxy group, 1 to 3 methyl groups, an ethyl group, and 1 to 3 fluorine atoms;
phenyl, benzyl, and phenethyl groups,
wherein the aromatic rings of the phenyl, benzyl and phenethyl groups may be substituted with 1 to 5 substituents Z,
wherein Z chosen from branched or unbranched ($C_{1-3}$)-alkyl or alkoxy, hydroxy, halogen trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkylsulfonyl, dimethylsulfamido, branched or unbranched ($C_{1-3}$)-alkoxycarbonyl, carboxyl, trifluoromethylsulfonyl, cyano, carbamoyl, sulfamoyl, and acetyl groups;
pyridyl and thienyl groups; and
$NR_5R_6$ groups,
wherein $R_5$ and $R_6$, together with the nitrogen atom to which they are attached, form a saturated or unsaturated, monocyclic or bicyclic, heterocyclic group having 4 to 10 ring atoms,
wherein the heterocyclic group contains at least one heteroatom chosen from oxygen, nitrogen, and sulphur, and may optionally be substituted with a substituent chosen from a branched or unbranched ($C_{1-3}$)-alkyl group, a hydroxy group, a trifluoromethyl group, and a fluorine atom; or $R_3$ and $R_4$, together with the nitrogen atom to which they are attached, form a saturated or unsaturated, monocyclic or bicyclic, heterocyclic group having 4 to 10 ring atoms,
wherein the heterocyclic group contains at least one heteroatom chosen from from oxygen, nitrogen, and sulphur, and may optionally be substituted with a substituent chosen from a branched or unbranched ($C_{1-3}$)-alkyl group, a hydroxy group, a trifluoromethyl group, and a fluorine atom;

or stereoisomers and salts thereof.

9. A compound of formula (V)

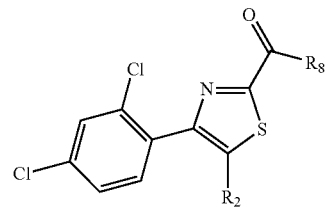

(V)

wherein
$R_2$ is chosen from:
a naphthyl group; and
phenyl, thienyl, pyridyl, and pyrimidinyl groups,
wherein the phenyl, thienyl, pyridyl, and pyrimidinyl groups may optionally be substituted with 1 to 4 substituents X,
wherein X is chosen from branched or unbranched ($C_{1-3}$)-alkyl or alkoxy, hydroxy, halogen, trifluoromethyl, trifluoromethylthio, trifluoromethoxy, nitro, amino, monoalkyl-($C_{1-2}$)-amino, dialkyl-($C_{1-2}$)-amino, monoalkyl-($C_{1-2}$)-amido, dialkyl-($C_{1-2}$)-amido, branched or unbranched ($C_{1-3}$)-alkoxycarbonyl, trifluoromethylsulfonyl, sulfamoyl, branched or unbranched alkyl-($C_{1-3}$)-sulfonyl, carboxyl, cyano, carbamoyl, branched or unbranched dialkyl-($C_{1-3}$)-aminosulfonyl, branched or unbranched monoalkyl-($C_{1-3}$)-aminosulfonyl, and acetyl groups; and $R_8$ is chosen from a hydroxy group, a branched or unbranched ($C_{1-4}$)-alkoxy group, a benzyloxy group, and a chlorine atom.

* * * * *

UNITED STATES PATENT AND TRADEMARK OFFICE
CERTIFICATE OF CORRECTION

PATENT NO.        : 7,342,032 B2
APPLICATION NO. : 10/490546
DATED             : March 11, 2008
INVENTOR(S)      : Lange et al.

It is certified that error appears in the above-identified patent and that said Letters Patent is hereby corrected as shown below:

On the Title Page, Item (57), delete the Abstract in its entirety and replace therewith:

--The present invention relates to a group of thiazole derivatives which are potent antagonists, agonists or partial agonists of the cannabinoid $CB_1$-receptor. The compounds have the general formula (I) wherein R and $R_1$-$R_4$ have the meanings given in the specification.

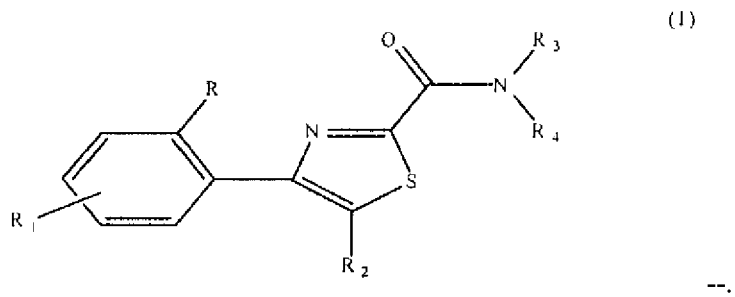

--.

In claim 1, column 12, line 24, "monoalkyl($C_{1-2}$)-amido," should read --monoalkyl-($C_{1-2}$)-amido,--.

In claim 2, column 13, lines 35-36, "($C_{1-10}$)-tricycloalkyl," should read --($C_{6-10}$)-tricycloalkyl,--.

In claim 3, column 14, line 32, "aikoxy," should read --alkoxy,--.

In claim 7, column 19, line 44, "substituents 7," should read --substituents Z,--.

In claim 8, column 20, line 32, "monoalkyl-($C_{1-2}$)amido," should read --monoalkyl-($C_{1-2}$)-amido,--.

In claim 8, column 21, lines 45-46, "halogen trifluoromethyl," should read --halogen, trifluoromethyl,--.

Signed and Sealed this

Ninth Day of November, 2010

David J. Kappos
*Director of the United States Patent and Trademark Office*